(12) United States Patent
Lee et al.

(10) Patent No.: US 10,098,804 B2
(45) Date of Patent: Oct. 16, 2018

(54) WALKING ASSISTANCE APPARATUS

(71) Applicant: Samsung Electronics Co., Ltd., Suwon-si, Gyeonggi-do (KR)

(72) Inventors: Minhyung Lee, Anyang-si (KR); Yongjae Kim, Seoul (KR); Jeonghun Kim, Hwaseong-si (KR); Youngdo Kwon, Yongin-si (KR); Se-Gon Roh, Suwon-si (KR); Youn Baek Lee, Suwon-si (KR); Jongwon Lee, Uiwang-si (KR); Byungjune Choi, Gunpo-si (KR); Hyun Do Choi, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 830 days.

(21) Appl. No.: 14/692,257

(22) Filed: Apr. 21, 2015

(65) Prior Publication Data

US 2015/0335515 A1 Nov. 26, 2015

(30) Foreign Application Priority Data

May 23, 2014 (KR) .................. 10-2014-0061991

(51) Int. Cl.
*A61H 3/00* (2006.01)
*A61H 1/02* (2006.01)
(Continued)

(52) U.S. Cl.
CPC ............. *A61H 3/008* (2013.01); *A61H 1/024* (2013.01); *A61H 1/0244* (2013.01); *A61H 3/00* (2013.01);
(Continued)

(58) Field of Classification Search
CPC .... A61H 1/024; A61H 1/0244; A61H 1/0262; A61H 3/008; A61H 3/04;
(Continued)

(56) References Cited

U.S. PATENT DOCUMENTS

2009/0306554 A1 12/2009 Yasuie
2009/0306564 A1* 12/2009 Hirata et al. .............. A61F 5/00
602/23
(Continued)

FOREIGN PATENT DOCUMENTS

KR 20110083143 A 7/2011
KR 20110103530 A 9/2011
(Continued)

*Primary Examiner* — Timothy Stanis
(74) *Attorney, Agent, or Firm* — Harness, Dickey & Pierce, P.L.C.

(57) ABSTRACT

A walking assistance apparatus for preventing offset occurring in between a rotating axis of a hip joint of a user and a rotating shaft of the walking assistance apparatus may be provided. The walking assistance apparatus includes a waist fixing apparatus configured to be fixed to a waist of a user, a connecting guide mounted at the waist fixing apparatus and configured to slide in an extension direction of the waist fixing apparatus and rotate on a rotating shaft extending in a vertical direction perpendicular to the extension direction, a rail unit mounted at one side of the connecting guide, the rail unit extending in a vertical direction, and a hip joint configured to slide along the rail unit.

20 Claims, 13 Drawing Sheets

(51) Int. Cl.
*A61F 5/01* (2006.01)
*B25J 9/00* (2006.01)

(52) U.S. Cl.
CPC .... *A61F 5/0125* (2013.01); *A61H 2201/0192* (2013.01); *A61H 2201/1215* (2013.01); *A61H 2201/164* (2013.01); *A61H 2201/165* (2013.01); *A61H 2201/1628* (2013.01); *A61H 2201/5007* (2013.01); *A61H 2201/5043* (2013.01); *A61H 2201/5058* (2013.01); *B25J 9/0006* (2013.01)

(58) Field of Classification Search
CPC ...... A61H 2201/1628; A61H 2003/007; A61F 5/0102; A61F 5/0125; B25J 9/0006
USPC ............................................. 602/16, 19, 23
See application file for complete search history.

(56) References Cited

U.S. PATENT DOCUMENTS

| | | |
|---|---|---|
| 2010/0036302 A1 | 2/2010 | Shimada et al. |
| 2010/0113989 A1* | 5/2010 | Matsuoka et al. ....... A61H 1/00 601/35 |
| 2011/0160626 A1 | 6/2011 | Takahashi et al. |

FOREIGN PATENT DOCUMENTS

| | | |
|---|---|---|
| KR | 20130038448 A | 4/2013 |
| KR | 20130045874 A | 5/2013 |

* cited by examiner

WALKING ASSISTANCE APPARATUS

CROSS-REFERENCE TO RELATED APPLICATION

This application claims priority under 35 U.S.C. § 119 to the Korean Patent Application No. 2014-0061991, filed on May 23, 2014, in the Korean Intellectual Property Office, the entire disclosure of which is incorporated herein by reference.

BACKGROUND

1. Field

Example embodiments of the present disclosure relate to walking assistance apparatuses.

2. Description of the Related Art

In general, a walking assistance apparatus, depending on the field at which the walking assistance apparatus is being used, may be used as an assistance apparatus configured to assist supporting weight and/or deteriorated muscular strength, or, when carrying a heavy load, may also be used as a reinforcing apparatus configured to amplify muscular strength of a user and/or support weight of the heavy load placed on the user.

SUMMARY

Therefore, it is an aspect of the present disclosure to provide walking assistance apparatuses capable of assisting walking of a user.

Additional aspects of the disclosure will be set forth in part in the description which follows and, in part, will be obvious from the description, or may be learned by practice of the disclosure.

According to an example embodiment, a walking assistance apparatus includes a waist fixing apparatus configured to be fixed to a waist of a user, a connecting guide mounted at the waist fixing apparatus, and configured to slide in an extension direction of the waist fixing apparatus and rotate on a rotating shaft extending in a vertical direction perpendicular to the extension direction, a rail unit mounted at one side of the connecting guide, the rail unit extending in a vertical direction, and a hip joint configured to slide along the rail unit.

According to some example embodiments, the rail unit may be spaced apart from the waist fixing apparatus.

According to some example embodiments, the rail unit and the connecting guide unit may be pivotally connected to each other.

According to some example embodiments, the walking assistance apparatus may further include a rail extended in a length direction of the waist fixing apparatus, and a sliding unit configured to slide along the rail.

According to some example embodiments, the connecting guide may be pivotally connected to the sliding unit.

According to some example embodiments, the connecting guide, the rail, and the sliding unit each may be provided at both sides of the rail unit.

According to some example embodiments, the walking assistance apparatus may further include a moving bracket configured to slide along the rail unit, and a connecting bracket configured to connect the moving bracket to the hip joint.

According to some example embodiments, the hip joint may be fixed to the connecting bracket, and the connecting bracket may be pivotally connected to the moving bracket.

According to some example embodiments, the walking assistance apparatus may further include a back rail at one side of the waist fixing apparatus and extending in the vertical directions, and a mounting unit configured to slide along the back rail and mount a driving source thereon.

According to some example embodiments, one side of a weight supporting unit may be mounted at the mounting unit, and the other side of the weight supporting unit may be mounted at the moving bracket.

According to some example embodiments, the weight supporting unit may be a flexible shaft.

According to some example embodiments, a length of the waist fixing apparatus is configured to be adjusted by a belt adjusting unit.

According to some example embodiments, the waist fixing apparatus may include a first waist fixing apparatus including a first gear unit at one side thereof, and a second waist fixing apparatus including a second gear unit at one side thereof.

According to some example embodiments, the walking assistance apparatus may further include a third gear unit at the belt adjusting unit and configured to be teeth-coupled with the first gear unit and the second gear unit.

According to some example embodiments, the waist fixing apparatus may have an accommodation unit provided with a back gear unit at an inner side surface thereof, and the back gear unit is configured to be selectively teeth-coupled with the third gear unit.

According to some example embodiments, rotation of the third gear may be limited as the third gear unit and the gear unit may be teeth-coupled to each other.

According to some example embodiments, when the belt adjusting unit is rotated in one direction or the other, the first waist fixing apparatus and the second waist fixing apparatus may draw near to each other or spaced apart from each other.

According to another example embodiment, a walking assistance apparatus includes a waist fixing apparatus configured to be fixed to a waist of a user, a rail unit mounted at the waist fixing apparatus through a connecting guide, a hip joint configured to slide along the rail unit in a vertical direction perpendicular to an extension direction of the waist fixing apparatus, a mounting unit at which a driving source is mounted, and a weight supporting unit configured to connect the mounting unit to the hip joint such that a weight of the mounting unit is delivered to the hip joint. The connecting guide may be configured to slide along a rail in an extension direction of the waist fixing apparatus, and the connecting guide and the waist fixing apparatus may be pivotally connected to each other.

According to some example embodiments, the waist fixing apparatus may be configured to adjust a length thereof.

According to some example embodiments, the walking assistance apparatus may further include a back rail extended in a vertical direction at one side of the waist fixing apparatus. The mounting unit may be configured to slide along the back rail.

According to some example embodiments, the rail unit and the connecting guide may be pivotally connected to each other.

According to some example embodiments, the waist fixing apparatus may be formed of flexible material.

As is apparent from the above, an offset being occurred in between a rotating axis of a hip joint of a user and a rotating shaft of a walking assistance apparatus may be mitigated or prevented.

BRIEF DESCRIPTION OF THE DRAWINGS

These and/or other aspects of the disclosure will become apparent and more readily appreciated from the following description of the example embodiments, taken in conjunction with the accompanying drawings of which.

DETAILED DESCRIPTION

Figure 1:
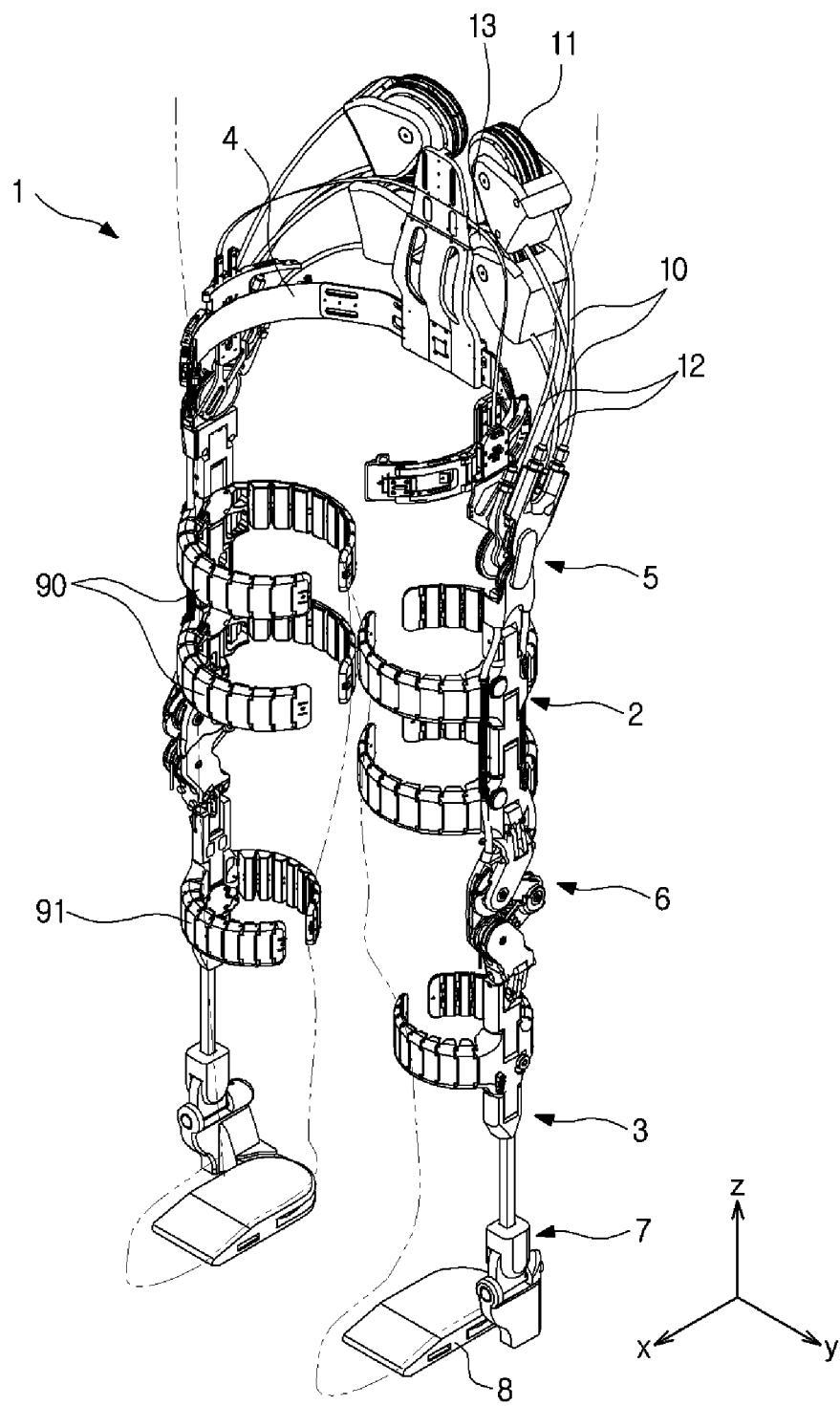
FIG. 1 is a drawing illustrating a walking assistance apparatus in accordance with one example embodiment of the present disclosure.

Various example embodiments will be described more fully hereinafter with reference to the accompanying drawings, in which some example embodiments are shown. The present disclosure may, however, be embodied in many different forms and should not be construed as limited to the example embodiments set forth herein. Rather, these example embodiments are merely provided so that this disclosure will be thorough and complete, and will fully convey the scope of example embodiments to those skilled in the art. In the drawings, the sizes and relative sizes of the various layers and regions may have been exaggerated for clarity. Like numerals refer to like elements throughout.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The term such as 'unit' or 'module' in this description indicates a unit or a member configured to process at least one function or perform at least one operation and may be implemented by hardware or software or a combination of hardware and software. A unit or module may advantageously be configured to reside on the addressable storage medium and configured to execute on one or more processors. Thus, a unit or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and units or modules may be combined into fewer components and units or modules or further separated into additional components and units or modules.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Expressions such as "at least one of," when preceding a list of elements, modify the entire list of elements and do not modify the individual elements of the list.

Hereinafter, some example embodiments will be explained in further detail with reference to the accompanying drawings.

FIG. 1 is a drawing illustrating a walking assistance apparatus in accordance with one example embodiment of the present disclosure.

Referring to FIG. 1, a walking assistance apparatus 1 in accordance with one example embodiment of the present disclosure may include a first frame 2 and a second frame 3 to support the weight of a user while being extended in a length direction of a leg of the user. The first frame 2 may be configured to support the femoral region of the user, and the second frame 3 may be configured to support the calf of the user.

The first frame 2 may be pivotally connected to a waist fixing apparatus 4 using a hip joint 5. The first frame 2 and the second frame 3 may be pivotally connected to each other by a knee joint 6. A foot structure 8, which is configured to be coupled to the foot of the user, may be connected to the second frame 3. The second frame 3 and the foot structure 8 may be pivotally connected to each other using an ankle joint 7.

The walking assistance apparatus 1 may further include a first driving source configured to supply a driving force to the hip joint 5 and the knee joint 6 and a control unit configured to control a motion of the walking assistance apparatus 1. A sensor may be provided at the foot structure 8, and motion information of the user detected by the sensor may be transmitted to the control unit. The control unit may be able to control the motions of the hip joint 5 and/or the knee joint 6 using the transmitted information. The walking assistance apparatus 1 may further include a second driving source to supply a driving force to the ankle joint 7.

The first frame 2 may pivot while having three degrees of freedom. Motions having three degrees of freedom may be performed by receiving a driving force or without a driving force. For example, a motion having one degree of freedom, for example, a motion of the first frame 2 pivoting on an x-axis may be performed by receiving a driving force, whereas motions having two degrees of freedom may be performed according to a motion of the user without receiving a driving force. The first frame 2 may pivot on a y-axis based on contraction and extension of a wire 10. The wire 10 may be wound around a pulley 11, which is connected to the driving source, and the wire 10 may be connected to the first frame 2 through the hip joint 5. As one example, as the pulley 11 is rotated by the driving source such that the wire 10 is being wound around the pulley 11, the first frame 2 may pivot on the y-axis in a first direction. When the wire 10 is being unwound from the pulley 11 as the pulley 11 is rotated by the driving source, the first frame 2 may pivot on the y-axis in a second direction opposite to the first direction.

The second frame 3 may pivot while having one degree of freedom with respect to the first frame 2. The second frame 3 pivotally connected to the first frame 2 by the knee joint 6 may pivot according to contraction and extension of a wire 12. The wire 12 may be wound around a pulley 13 connected to the driving source, and the wire 12 may be connected to the second frame 3 through the knee joint 6.

As one example, as the pulley 13 is rotated by the driving source such that the wire 12 is wound around the pulley 13, the second frame 3 may pivot on the y-axis in a first direction. When the wire 12 is being unwound from the pulley 13 as the pulley 13 is rotated by the driving source, the second frame 3 may pivot in a second direction opposite to the first direction.

The foot structure 8 may pivot while having three degrees of freedom with respect to the second frame 3. The foot structure 8 and the second frame 3 may be pivotally connected to each other by the ankle joint 7. The foot structure 8 and/or the second frame 3 may pivot on the ankle joint 7 according to movement of a user without using driving force. The foot structure 8 and/or the second frame 3 may pivot on the ankle joint 7 by a driving force from the driving source.

A first fixing apparatus 90 may be connected to the first frame 2. The first fixing apparatus 90 may mount the first frame 2 at the femoral region of a user by surrounding the femoral region of the user. A second fixing apparatus 91 may be connected to the second frame 3. The second fixing apparatus 91 may mount the second frame 3 at the calf of a user by surrounding the calf of the user.

As a user wears the walking assistance apparatus 1, the first frame 2 and/or the second frame 3 may be extended in a length direction of the leg of the user. The first frame 2 and/or the second frame 3 may include a plurality of links, which provide connection between the first frame 2 and the second frame 3. The plurality of links may be formed of rigid material. The first frame 2 and/or the second frame 3 may include a plurality of links providing pivotally connection between the first frame 2 and the second frame 3 so as to be flexibly bent according to motions and curves of the body of the user, and to stably support the weight of the user.

Hereinafter, the structures of the hip joint and the waist fixing apparatus of the walking assistance apparatus in accordance with one example embodiment of the present disclosure will be described in detail by referring to the drawings.

Figure 2:
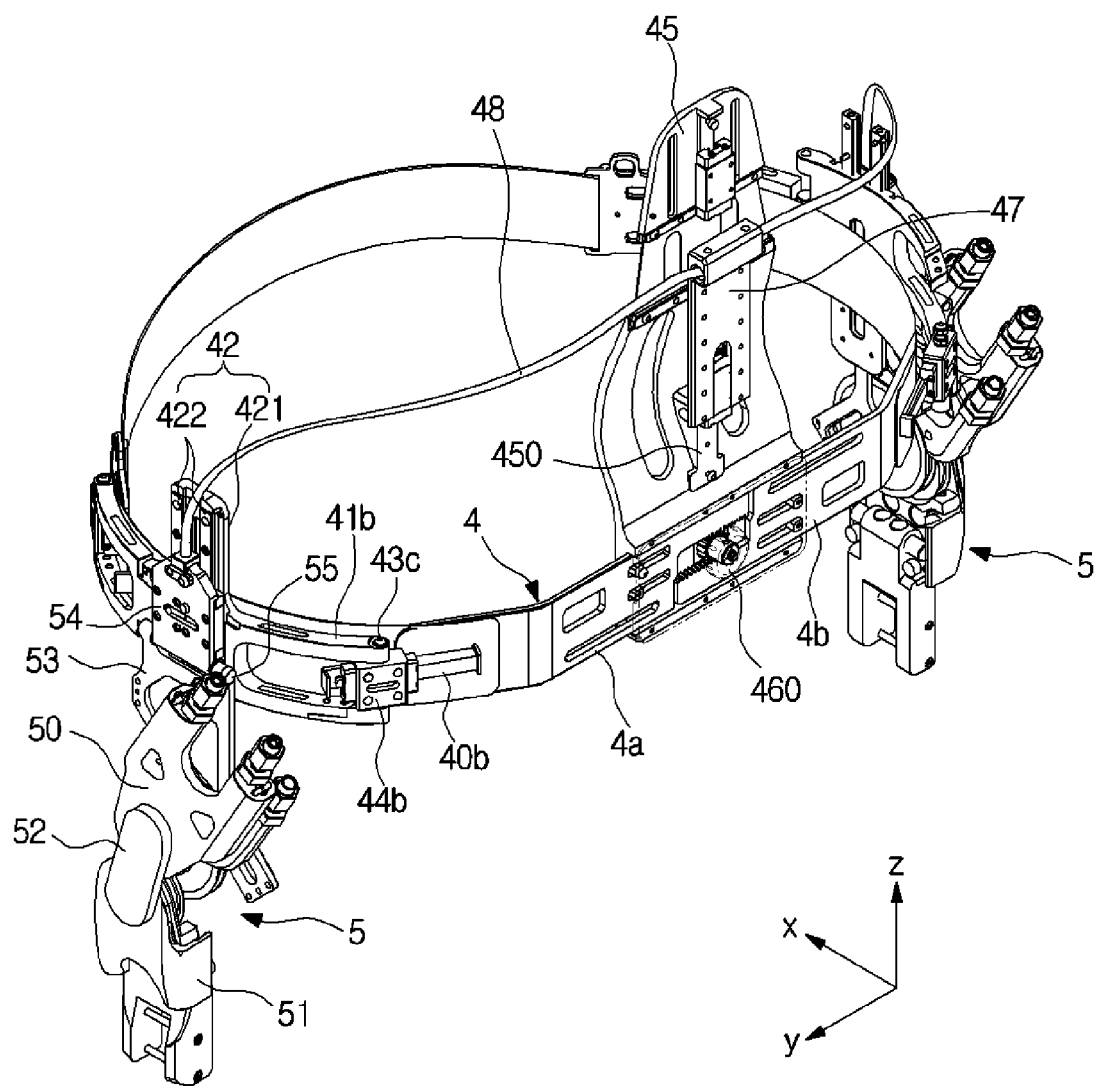
FIG. 2 is a perspective view illustrating a hip joint of the walking assistance apparatus in accordance with one example embodiment of the present disclosure.
Figure 3:
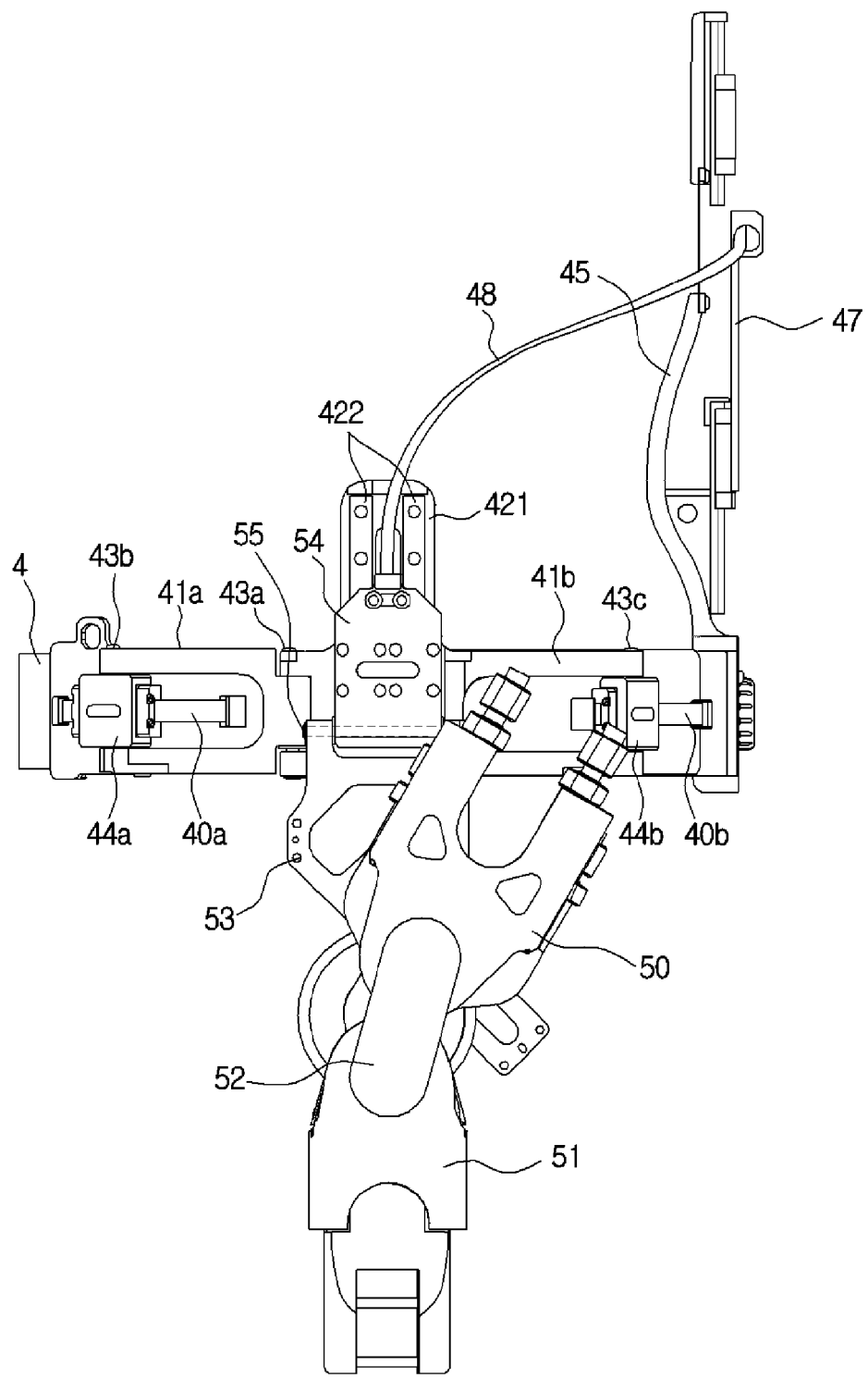
FIG. 3 is a side view illustrating the hip joint of the walking assistance apparatus in accordance with one example embodiment of the present disclosure.
Figure 4:
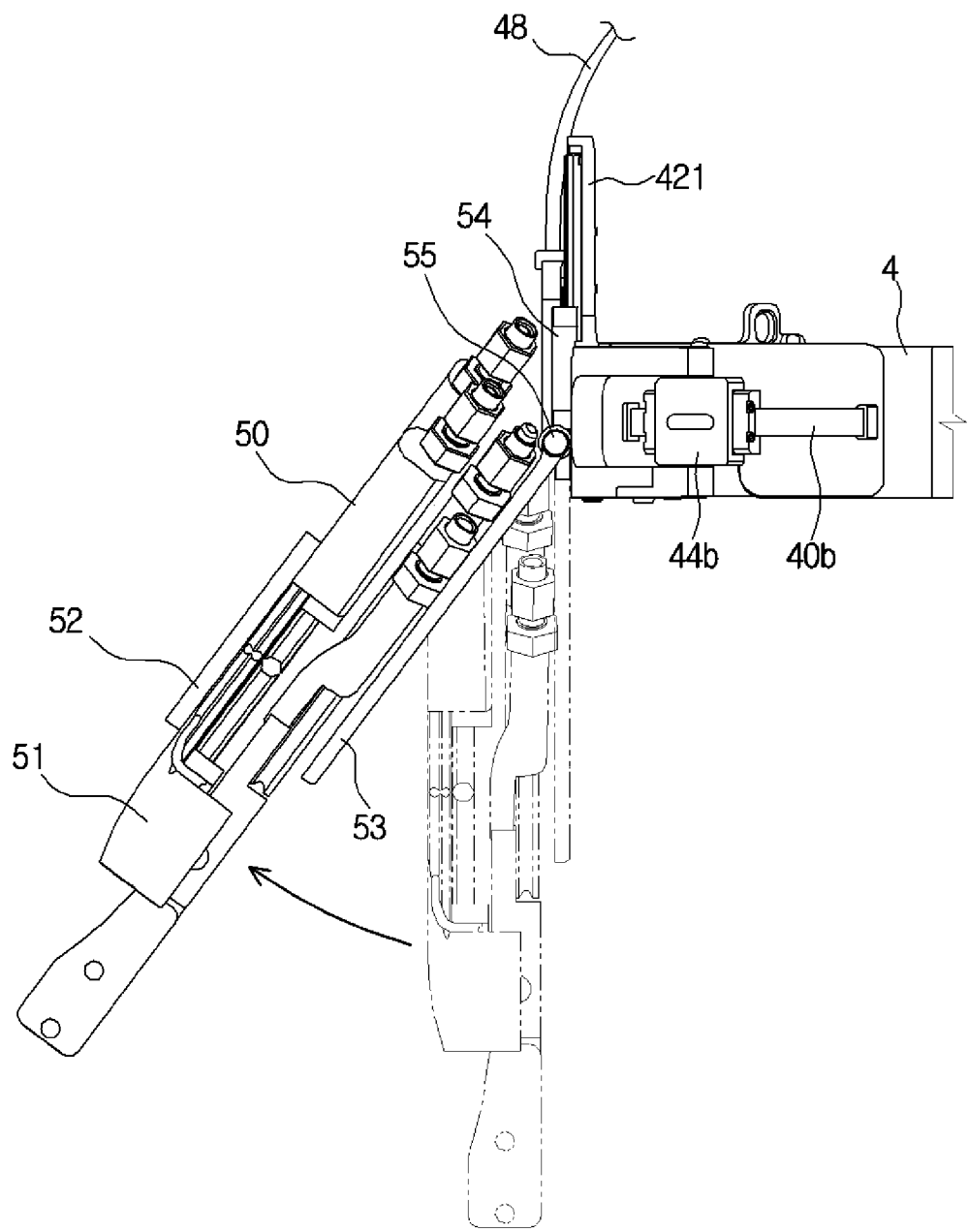
FIG. 4 is a drawing illustrating a motion of the hip joint when a frame of the walking assistance apparatus in accordance with one example embodiment of the present disclosure pivots on an x-axis.
Figure 5:
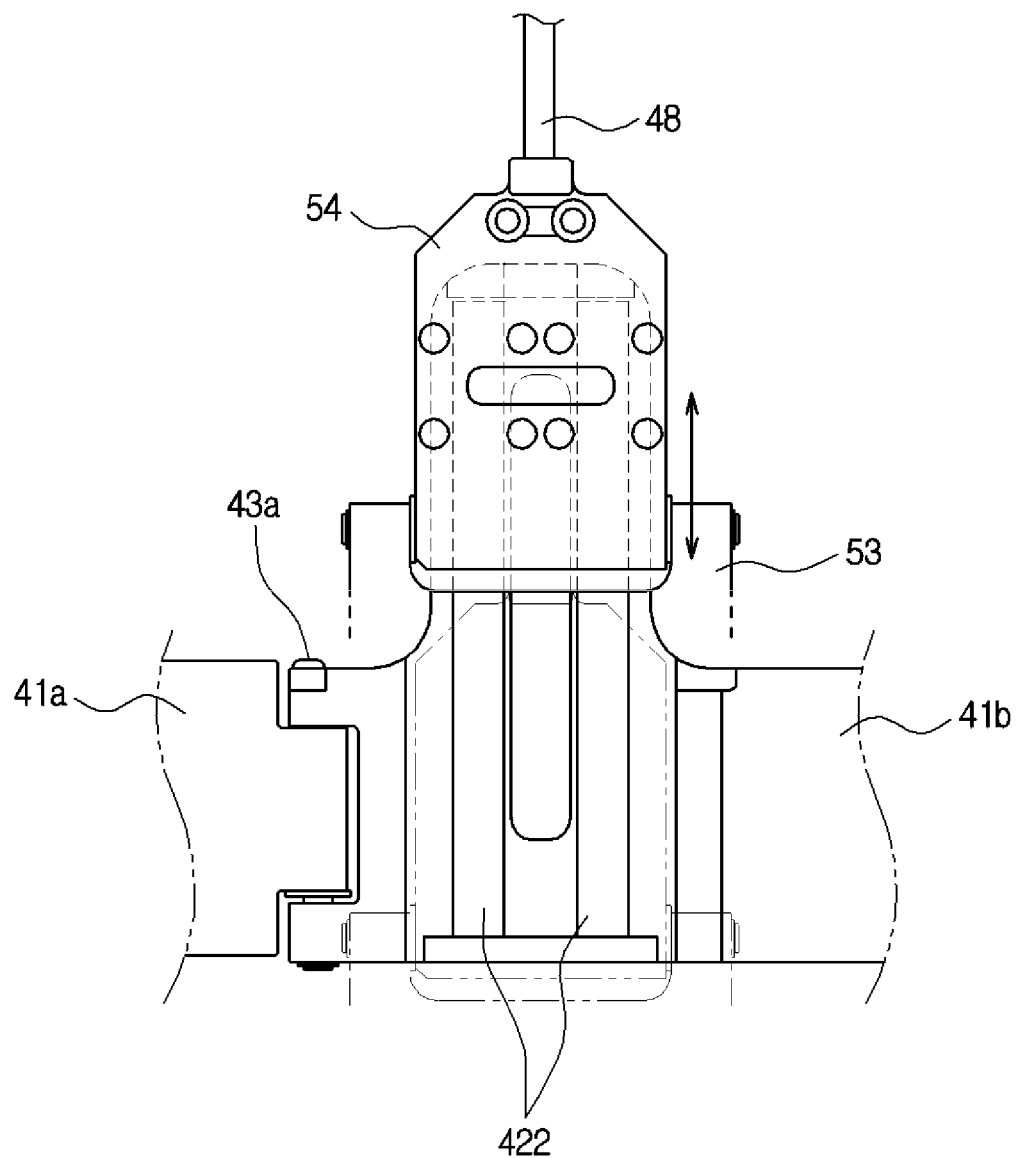
FIG. 5 is a drawing illustrating a moving bracket and a rail of the walking assistance apparatus in accordance with one example embodiment of the present disclosure.

FIG. 2 is a perspective view illustrating the hip joint of the walking assistance apparatus in accordance with one example embodiment of the present disclosure, FIG. 3 is a side view illustrating the hip joint of the walking assistance apparatus in accordance with one example embodiment of the present disclosure. FIG. 4 is a drawing illustrating a motion of the hip joint when a frame of the walking assistance apparatus in accordance with one example embodiment of the present disclosure pivots on an x-axis. FIG. 5 is a drawing illustrating a moving bracket and a rail of the walking assistance apparatus in accordance with one example embodiment of the present disclosure.

Referring to FIG. 2 to FIG. 5, the frames 2 and 3 of the walking assistance apparatus 1 in accordance with one example embodiment of the present disclosure may perform a pitch movement in which the leg of a user wearing the walking assistance apparatus 1 moves in forward/backward directions, a roll movement in which the leg of a user wearing the walking assistance apparatus 1 moves in left/right directions, and a yaw movement in which the leg of a user wearing the walking assistance apparatus 1 rotates on a direction of the leg being extended by use of the structure of the hip joint 5 and the waist fixing apparatus 4.

Hereinafter, the structures of the waist fixing apparatus 4 and the hip joint 5 will be described in connection with a roll movement, which is performed as the first frame 2 connected to the hip joint 5 pivots on the x-axis, a pitch movement, which is performed as the first frame 2 pivots on the y-axis, and a yaw movement, which is performed as the first frame 2 pivots on a z-axis.

The waist fixing apparatus 4 may be formed of flexible material so as to be closely and flexibly attached to the body of a user.

The hip joint 5 may include a first joint 50 connected to the waist fixing apparatus 4, a second joint 51 connected to the first frame 2, and a link 52 connecting the first joint 50 to the second joint 51. The first joint 50 and the second joint 51 may be pivoted by the wire 10 connected to the driving source. As the second joint 51 pivots with respect to the first joint 50, the first frame 2 connected to the second joint 51 may pivot on the y-axis.

The first joint 50 may be connected to the waist fixing apparatus 4 so as to pivot on the x-axis. A moving bracket 54 may be provided at the waist fixing apparatus 4, and the moving bracket 54 and the first joint 50 may be connected to each other using a connecting bracket 53. The connecting bracket 53 may be connected to the moving bracket 54 so as to rotate on a rotating shaft 55. As a user wearing the walking assistance apparatus 1 moves the leg of the user in left/right directions, the connecting bracket 53 may rotate on the rotating shaft 55, and thus the frames 2 and 3 may pivot on the x-axis in accordance with the movements of the leg of the user.

A rail unit 42 along which the moving bracket 54 may slide may be provided at the waist fixing apparatus 4. The rail unit 42 includes a rail guide 421 mounted at the waist fixing apparatus 4, and a first rail 422 extended in a direction of the z-axis on the rail guide 421. The moving bracket 54 may be provided so as to slide along the first rail 422 in the z-axis direction.

When a user wearing the walking assistance apparatus 1 moves the leg of the user in left/right directions, an offset, which is present in between a rotating axis of a hip joint positioned inside the body of the user and the rotating shaft 55 connecting the connecting bracket 53 to the moving bracket 54 may be compensated so that the movements of the user may be naturally performed, thereby enhancing the usability of the walking assistance apparatus 1.

Figure 6:
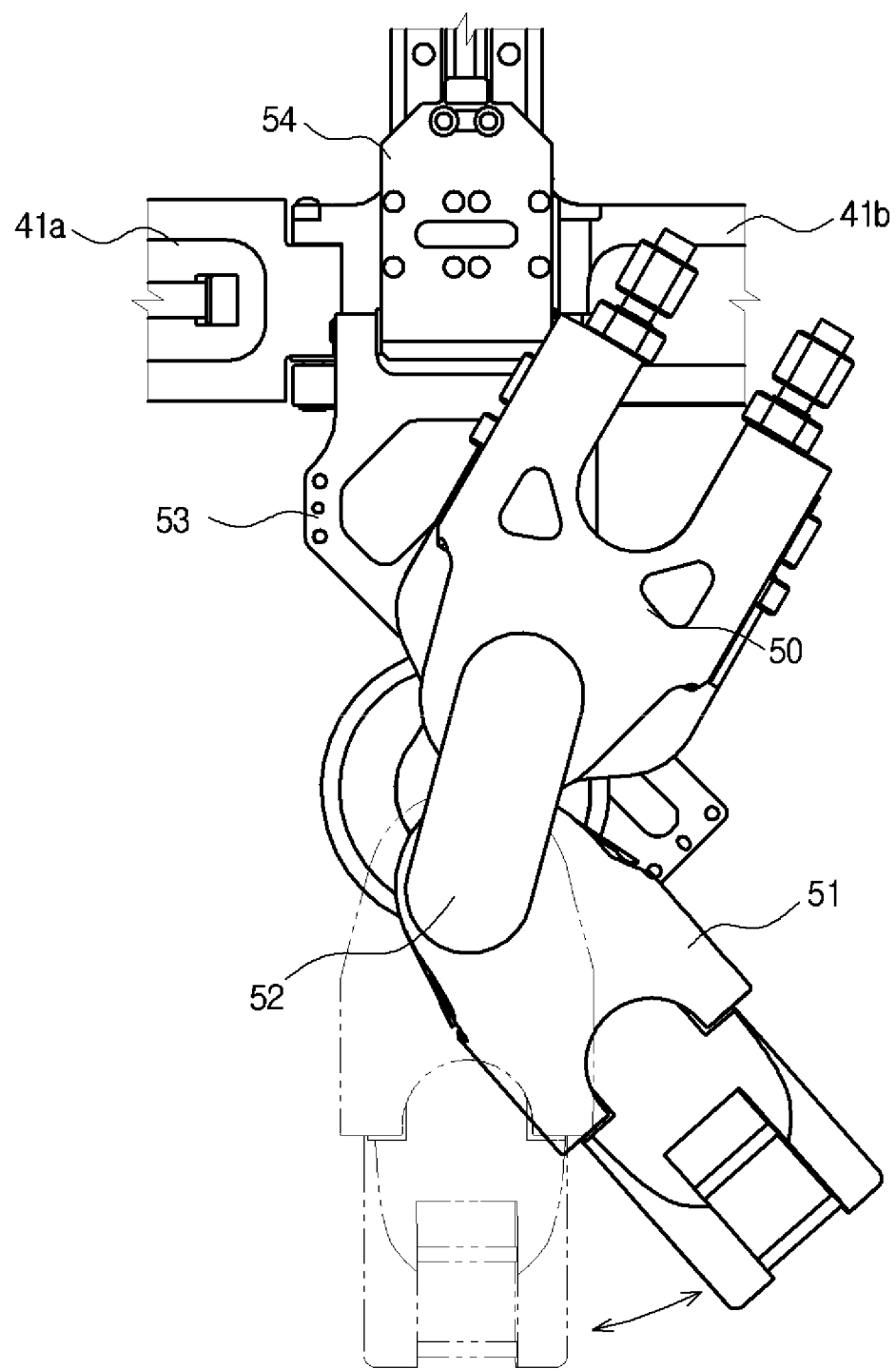
FIG. 6 is a drawing illustrating a motion of the hip joint when the hip joint of the walking assistance apparatus in accordance with one example embodiment of the present disclosure pivots on a y-axis.

FIG. 6 is a drawing illustrating a motion of the hip joint when the hip joint of the walking assistance apparatus in accordance with one example embodiment of the present disclosure pivots on a y-axis.

Referring to FIG. 6, the second joint 51 of the hip joint 5 in accordance with one example embodiment of the present disclosure may pivot on the y-axis by the wire 10 connected to the driving source. The first frame 2 connected to the second joint 51 may pivot on the y-axis along with the second joint 51. As the hip joint 5 pivots on the y-axis based on the driving force delivered from the driving source, a user having difficulty in walking may smoothly perform the pitch movement.

Figure 7:
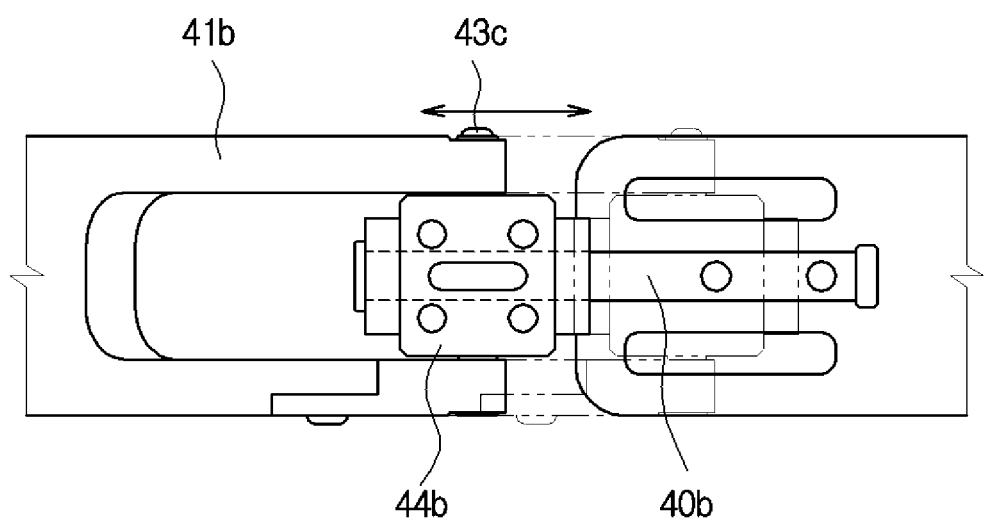
FIG. 7 is a drawing illustrating a motion of a waist fixing apparatus when the frame of the walking assistance apparatus in accordance with one example embodiment of the present disclosure pivots on a y-axis.
Figure 8:
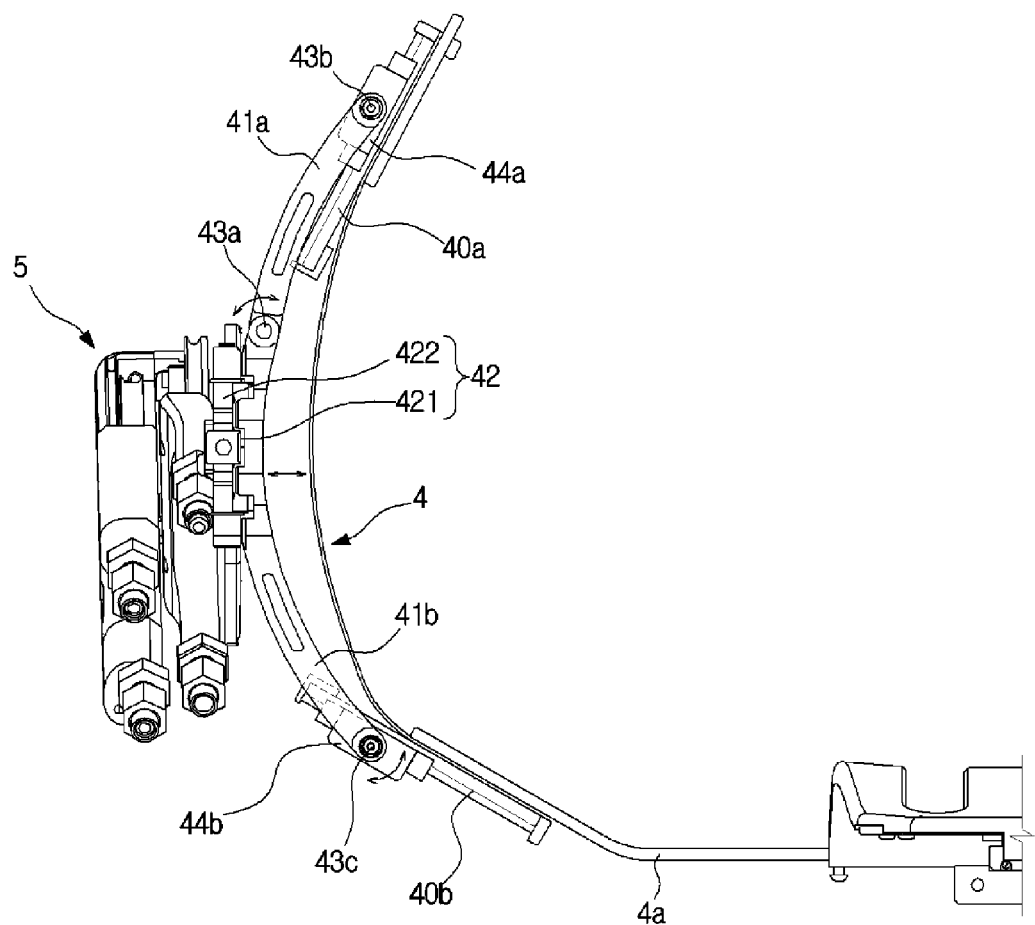
FIG. 8 is a top view illustrating the hip joint and the waist fixing apparatus of the walking assistance apparatus in accordance with one example embodiment of the present disclosure.

FIG. 7 is a drawing illustrating a motion of a waist fixing apparatus when the frame of the walking assistance apparatus in accordance with one example embodiment of the present disclosure pivots on a y-axis, and FIG. 8 is a top view illustrating the hip joint and the waist fixing apparatus of the walking assistance apparatus in accordance with one example embodiment of the present disclosure.

Referring to FIG. 7 and FIG. 8, the rail guide 421 may be provided so as to slide along second rails 40a and 40b extended in a length direction of the waist fixing apparatus 4. The second rails 40a and 40b may be provided at left (or front) and right (or rear) sides of the rail unit 42, respectively. On the second rails 40a and 40b, sliding units 44a and 44b configured to slide along the second rails 40a and 40b may be provided, respectively. The rail guide 421 may be connected to the sliding units 44a and 44b by connecting guides 41a and 41b. The sliding units 44a and 44b configured to slide along the second rails 40a and 40b and the connecting guides 41a and 41b being connected to the sliding units 44a and 44b may be provided at the both left (or front) and right (or rear) sides of the rail unit 42, respectively. As the connecting guides 41a and 41b slide along the rails 40a and 40b, the rail guide 421 may slide along an extension direction of the rails 40a and 40b. As the rail guide 421 to which the hip joint 5 is connected may slide in the extension direction of the waist fixing apparatus 4, an operating range of the first frame 2 may be widened with regard to the yaw movement of the first frame 2.

The connecting guides 41a and 41b may be connected to the sliding units 44a and 44b so as to pivot on rotating shafts 43b and 43c. At least one of the connecting guides 41a and 41b may be connected to the rail guide 421 so as to pivot on the rotating shaft 43a. The rotating shafts 43a, 43b, and 43c may extend perpendicular to the extension direction of the waist fixing apparatus 4. As the connecting guides 41a and 41b are connected so as to pivot on the rotating shafts 43a, 43b, and 43c, the offset in between the rotating axis of the yaw movement of a user and the rotating shaft of the walking assistance apparatus 1 may be compensated.

The hip joint 5 of the walking assistance apparatus 1 may be spaced apart from the waist fixing apparatus 4 by the movements of a user. As a user wearing the walking assistance apparatus 1 performs the yaw movement as to rotate the leg of the user on the z-axis, the sliding units 44a and 44b may slide along the rails 40a and 40b according to the movements of the user, and the connecting guides 41a and 41b may rotate on the rotating shafts 43a, 43b, and 43c. The hip joint 5 may be naturally spaced apart from the waist fixing apparatus 4 by the yaw movement of the user, and thus the yaw movement of the user may be comfortably performed without being interfered by a particular portion of the walking assistance apparatus 1.

As one example, when a user rotates the leg of the user in a clockwise direction on the z-axis, the connecting guides 41a and 41b rotates on the rotating shafts 43a, 43b, and 43c in a clockwise direction, and the sliding units 44a and 44b may slide forward along the second rails 40a and 40b. As the user rotates the leg of the user in a counter-clockwise direction, the connecting guides 41a and 41b rotates on the rotating shafts 43a, 43b, and 43c in a counter-clockwise direction, and the sliding units 44a and 44b may slide backward along the second rails 40a and 40b. Thus, the yaw movement of a user wearing the walking assistance apparatus 1 may be naturally performed.

The structure in which the hip joint 5 is spaced apart from the waist fixing apparatus 4 may secure the margin in the degree of freedom even at the time of the pitch movement or the roll movement of the user wearing the walking assistance apparatus 1. While the waist fixing apparatus 4 is fixed to the waist of a user, the hip joint 5 may be spaced apart from the waist fixing apparatus 4 according to the pitch, roll, or yaw movement of the user, and thus the movements of the user may be naturally performed, and the hip joint 5 may also move according to the shape of each various users.

Figure 9:
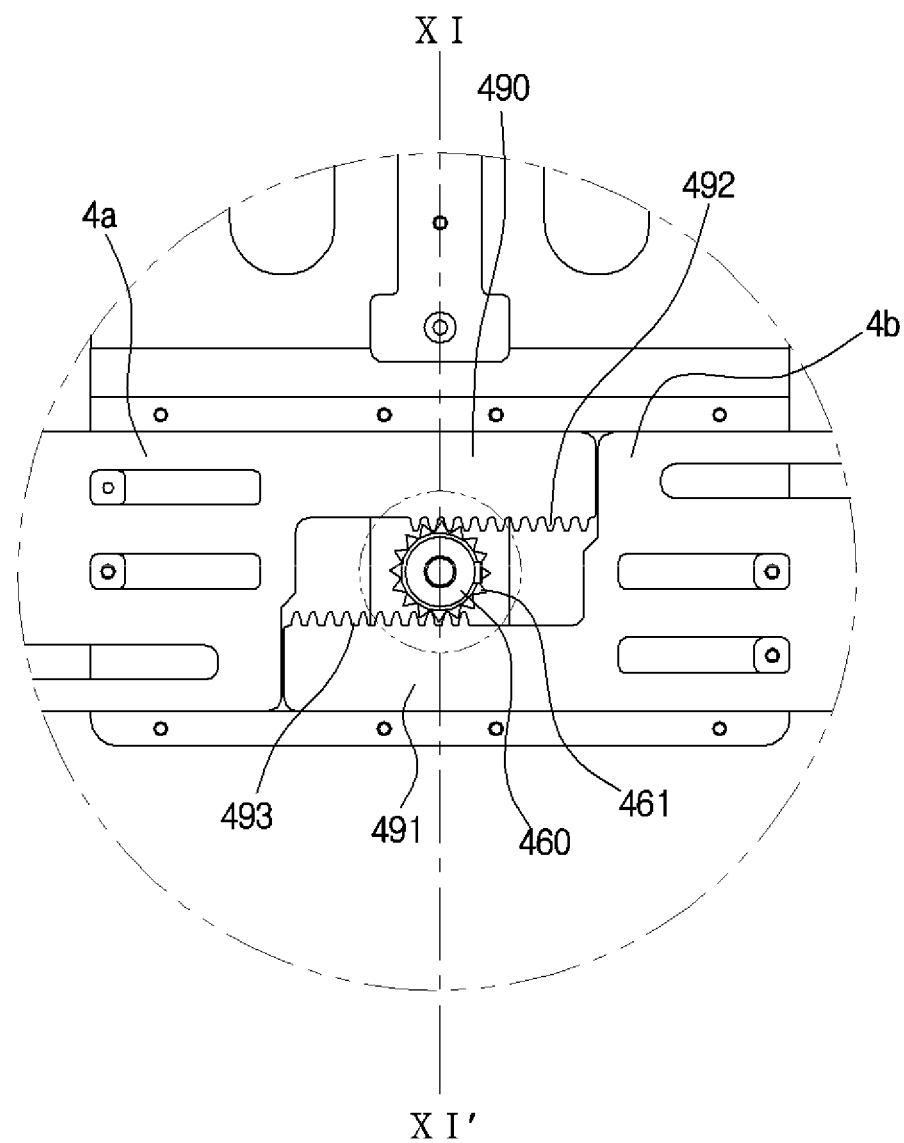
FIG. 9 is a drawing illustrating a belt adjusting unit of the walking assistance apparatus in accordance with one example embodiment of the present disclosure.
Figure 10:
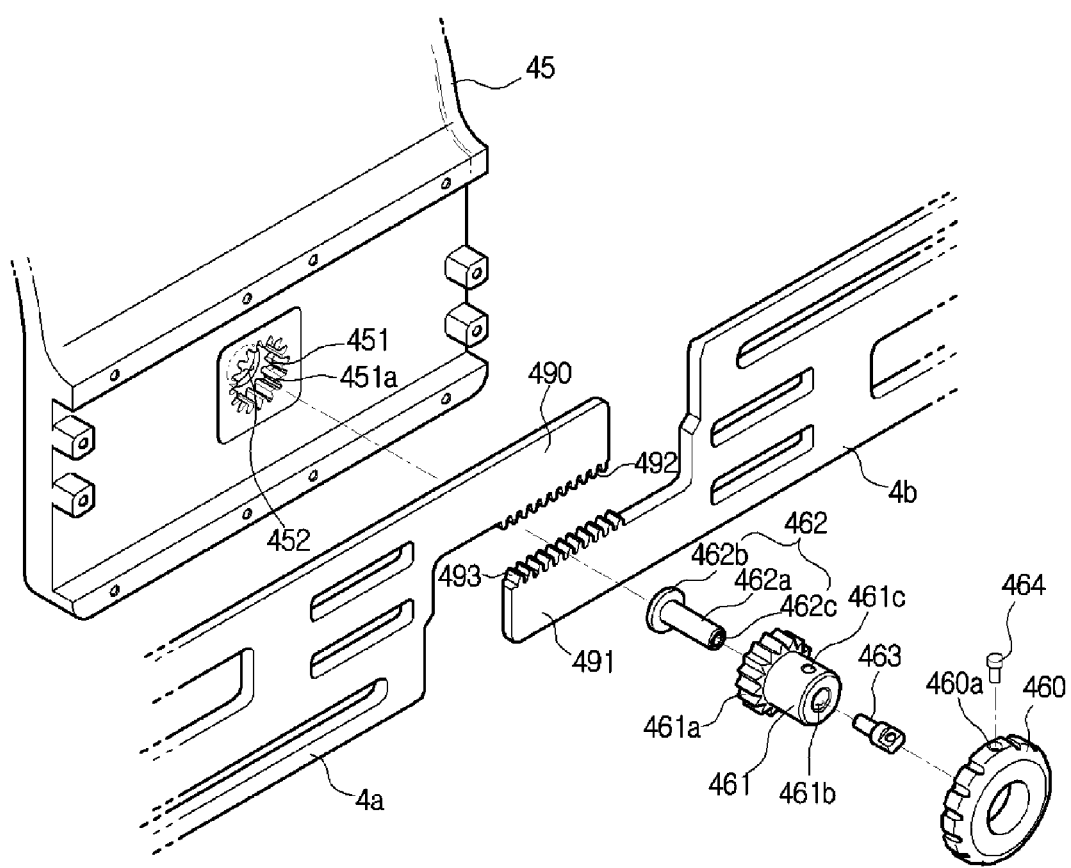
FIG. 10 is an exploded perspective view illustrating the belt adjusting unit of the walking assistance apparatus in accordance with one example embodiment of the present disclosure.
Figure 11:
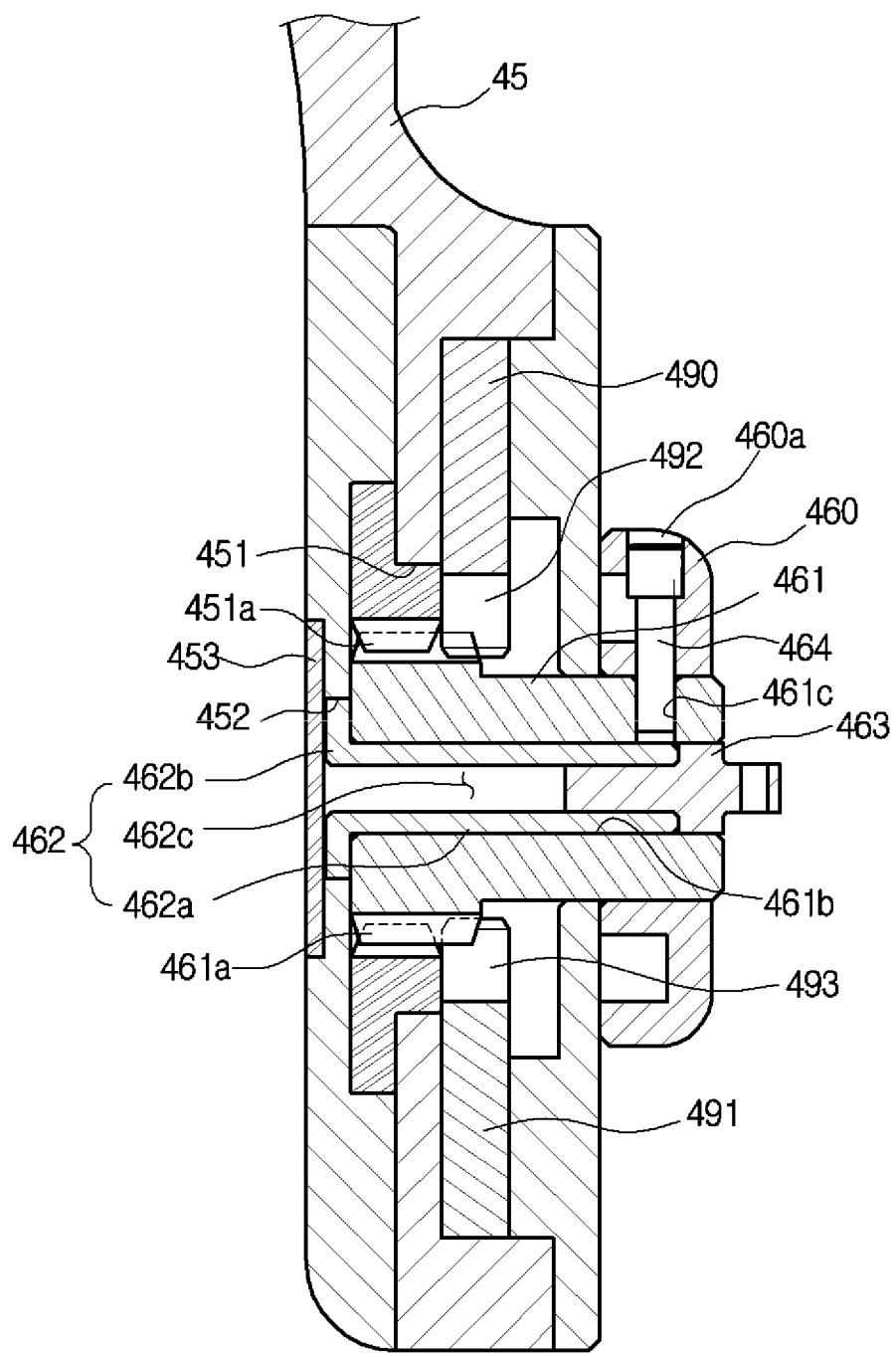
FIG. 11 and FIG. 12 are cross sectional views taken along line XI-XI' of FIG. 9.
Figure 12:
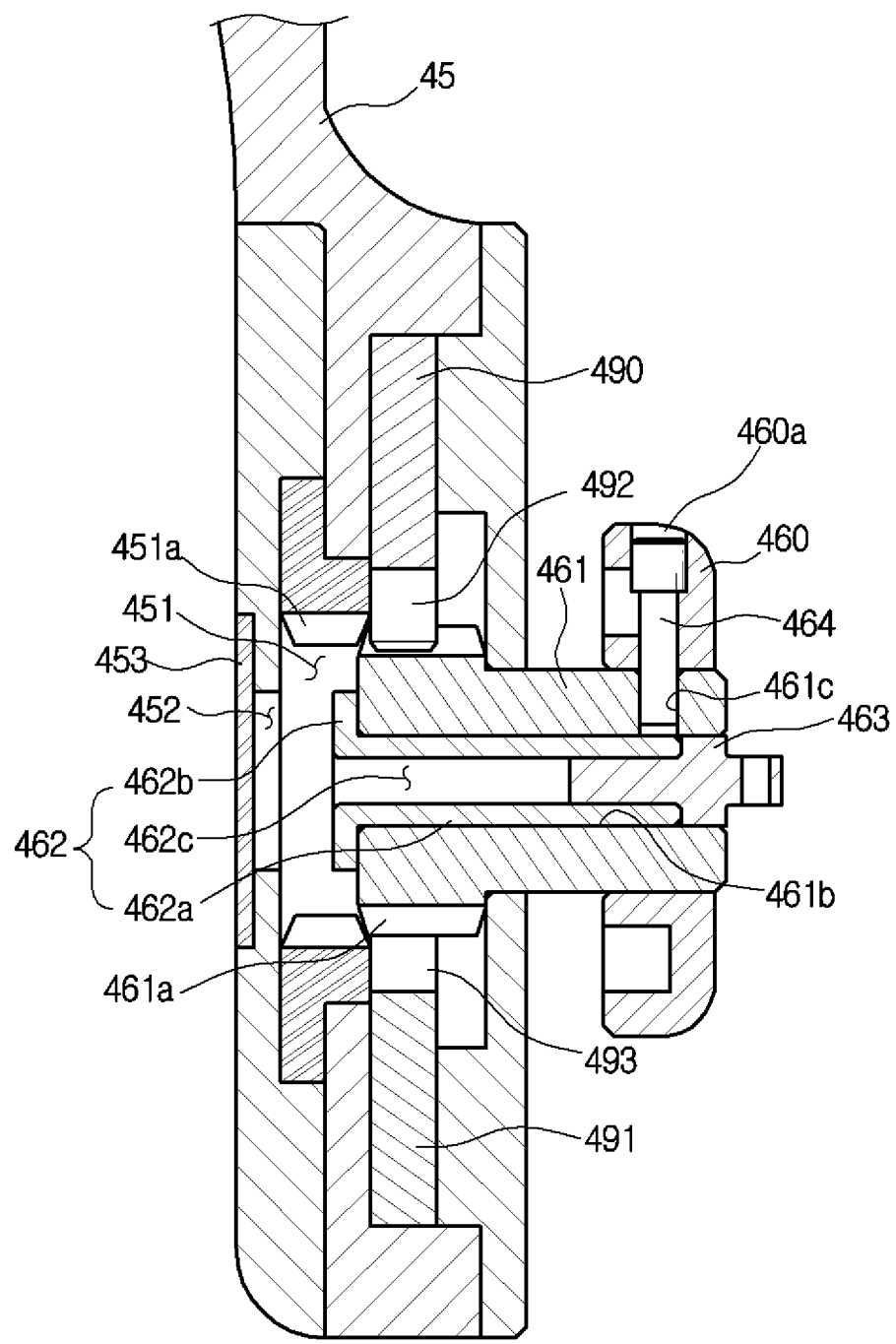

FIG. 9 is a drawing illustrating a belt adjusting unit of the walking assistance apparatus in accordance with one example embodiment of the present disclosure. FIG. 10 is an exploded perspective view illustrating the belt adjusting unit of the walking assistance apparatus in accordance with one example embodiment of the present disclosure. FIG. 11 and FIG. 12 are cross sectional views taken along line XI-XI' of FIG. 9.

Referring to FIG. 2 and FIG. 9 to FIG. 12, the waist fixing apparatus 4 may include a first waist fixing apparatus 4a and a second waist fixing apparatus 4b. The first waist fixing apparatus 4a and the second waist fixing apparatus 4b may be disposed at left and right sides of a user wearing the walking assistance apparatus 1, respectively, and may be provided in the shape of a single belt. The first waist fixing apparatus 4a and the second waist fixing apparatus 4b may be provided such that the entire length may be shortened or lengthened while moving in the extension direction of the waist fixing apparatus 4 by a belt adjusting unit 460 positioned at, for example, a center of the back of the user. The belt adjusting unit 460 may be exposed to an outside of the waist fixing apparatus 4 so that the length of the belt can be adjusted by the user.

A first extension portion 490 including a first gear unit 492 formed at one side thereof may be provided at one end of the first waist fixing apparatus 4a. A second extension portion 491 including a second gear unit 493 formed at one side thereof may be provided at one end of the second waist fixing apparatus 4b. As the first waist fixing apparatus 4a and the second waist fixing apparatus 4b are disposed as to form a linear line, the first gear unit 492 and the second gear unit 493 may be provided as to be spaced apart by a desired (or alternatively, predetermined) distance while facing each other.

A connecting unit 461 provided with a third gear unit 461a at an outer side thereof may be coupled to the belt adjusting unit 460, and the third gear unit 461a may be teeth-coupled into the first gear unit 492 and the second gear unit 493 while being positioned in between the first gear unit 492 and the second gear unit 493. When the belt adjusting unit 460 rotates in a clockwise or counter-clockwise direction, the first waist fixing apparatus 4a and the second waist fixing apparatus 4b may be approached with respect to each other or spaced apart from each other, and thus the entire length may be shortened or lengthened.

A hole 461b extending in a length direction of the connecting unit 461 may be formed at the connection unit 461, and a coupling unit may be inserted into the hole 461b. The coupling unit may include a first coupling unit 462 being inserted into the hole 461b through one side of the hole 461a and a second coupling unit 463 being inserted into the hole 461b through the other side of the hole 461b. The first coupling unit 462 and the second coupling unit 463 may be inserted into the hole 461b through the one side and the other side of the hole 461b and then be fixed.

The first coupling unit 462 may include a body 462a penetrated through the hole 461b and a head 462b having a larger cross-sectional diameter compared with a diameter of the hole 461b. One portion of the second coupling unit 463 may be inserted into a hole 462c formed along a length direction of the body 462a.

The belt adjusting unit 460 may be coupled into the connecting unit 461 using a fixing member 464. A hole 460a into which the fixing member 464 may be inserted is formed at the belt adjusting unit 460, and a hole 461c corresponding to the hole 460a formed at the belt adjusting unit 460 may be formed at the connecting unit 461. The fixing member 464 may be inserted into the holes 460a and 461c formed at the belt adjusting unit 460 and the connecting unit 461, respectively, and fix the belt adjusting unit 460 to the connecting unit 461. A first accommodation unit 451 at which the third gear unit 461a is accommodated may be provided at one surface of a back rail guide 45. A back gear unit 451a corresponding to the third gear unit 461a may be formed at the first accommodation unit 451. When the third gear unit 461a and the back gear unit 451a are teeth-coupled with respect to each other while the third gear unit 461a is accommodated at the first accommodation unit 451, the connecting unit 461 may be fixed without being rotated. A second accommodation unit 452 in which at least one portion of the head 462b is accommodated may be formed at one side of the first accommodation unit 451. The second accommodation unit 452 may be provided as the first accommodation unit 451 is concavely caved in.

A magnet 453 may be mounted at one of the second accommodation unit 452 and the head 462b, and a metallic member to be pulled by the magnet 453 may be mounted at the other one of the second accommodation unit 452 and the head 462b. Hereinafter, an example embodiment in which the magnet 453 is provided at the second accommodation unit 452 and the metallic member is provided at the head 462a will be described.

As the head 462b is accommodated at the second accommodation unit 452, as long as no other external force is exerted, the head 462b may be fixed to the second accommodation unit 452 by the magnetic force of the magnet 453. By having the head 462b fixed using the magnet 453 while being accommodated at the second accommodation unit 452, the belt length adjusting structure may be implemented in a thinner manner.

When a user presses the belt adjusting unit 460 such that the third gear 461a or the head 462b is accommodated at the first accommodation unit 451 or the second accommodation unit 452, respectively, one portion of the third gear 461a may be teeth-coupled into the back gear unit 451a formed at an inner side of the first accommodation unit 451.

For example, one portion of the front of the third gear unit 461a may be teeth-coupled into the back gear unit 451a, and one portion of a rear of the third gear unit 461a may be teeth-coupled into the first gear unit 492 and the second gear unit 493. As the one portion of the third gear unit 461a is inserted into the first accommodation unit 451 and then teeth-coupled into the gear unit 451a formed at the inner side of the first accommodation unit 451, the third gear unit 461a may be fixed so as not to rotate. Through the above, the belt adjusting unit 460 may be fixed in a non-rotatable manner.

As the above, a user, after properly adjusting the entire length of the waist fixing apparatus 4 by rotating the belt adjusting unit 460, may press the belt adjusting unit 460 to fix the waist fixing apparatus 4 such that the entire length of the waist fixing apparatus 4 is not shortened or lengthened any further.

When a user pulls the belt adjusting apparatus 460, the third gear unit 461a and the head 462a may be exited from the first accommodation unit 451 and the second accommodation unit 452, respectively. At this time, the third gear unit 461a is not teeth-coupled into the back gear unit 451a, while may be able to teeth-coupled into the first gear unit 492 and the second gear unit 493. In a state when the third gear unit 461a is teeth-coupled into the first gear unit 492 and the second gear unit 493, when a user rotates the belt adjusting unit 460 in a clockwise or counter-clockwise direction, the entire length of the waist fixing apparatus 4 may be shortened or lengthened.

As one example, when the belt adjusting unit 460 rotates in a clockwise direction, the first waist fixing apparatus 4a moves toward the second waist fixing apparatus 4b, and the second waist fixing apparatus 4b moves toward the first waist fixing apparatus 4a, thereby shortening the entire length of the waist fixing apparatus 4. When the belt adjusting unit 460 rotates in a counter-clockwise direction, the first waist fixing apparatus 4a moves away from the second waist fixing apparatus 4b, and the second waist fixing apparatus 4b moves away from a side of the first waist fixing apparatus 4a, thereby lengthening the entire length of the waist fixing apparatus 4.

A user, by manipulating the belt adjusting unit 460, may adjust the rotating shaft of the hip joint 5 mounted at each of the first waist fixing apparatus 4a and the second waist fixing apparatus 4b to correspond to the rotating axis of the hip joint of the pitch movement that is positioned at an inside the body of the user. As described above, the position of the hip joint 5 varies according to the physical characteristics of each user. According to some example embodiments of the present disclosure, a user wearing the walking assistance apparatus 1 may individually adjust a position the hip joint 5 according to the physical characteristics of the user to achieve more comfortable posture for walking.

The first waist fixing apparatus 4a and the second waist fixing apparatus 4b may simultaneously move in association with the belt adjusting unit 460. The first waist fixing apparatus 4a and the second waist fixing apparatus 4b each may individually move in association with a respective belt adjusting unit.

Figure 13:
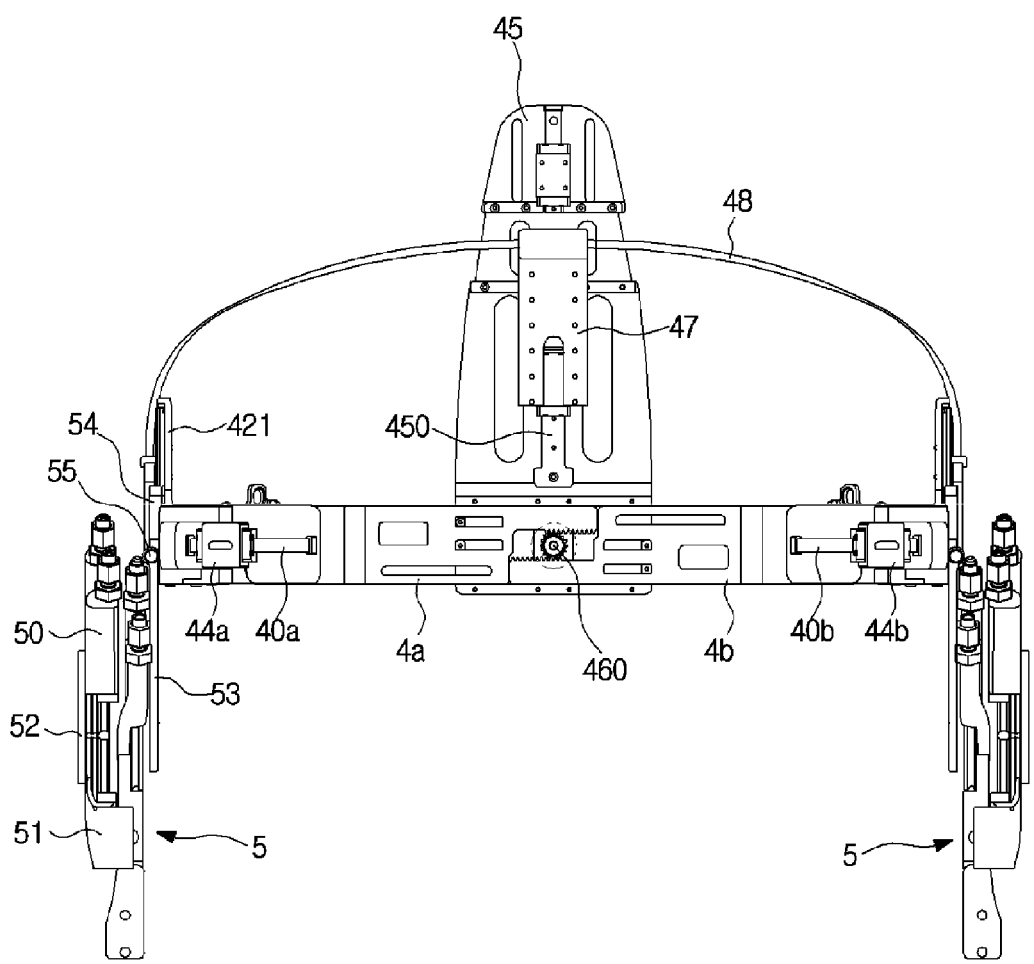
FIG. 13 is a rear side view illustrating the hip joint and the waist fixing apparatus in accordance with another example embodiment of the present disclosure seen.

FIG. 13 is a rear side view illustrating the hip joint and the waist fixing apparatus in accordance with another example embodiment of the present disclosure seen.

Referring to FIG. 13, the back rail guide 45 may be provided at one side of the waist fixing apparatus 4, and a back rail 450 extended in the z-axis may be provided at the back rail guide 45. The walking assistance apparatus 1 may include a mounting unit 47 at which an electrical apparatus (e.g., a driving source) configured to pivot the frames 2 and 3 is mounted. The mounting unit 47 may slide in the z-axis along the back rail 450.

A weight supporting unit 48 may be mounted at the mounting unit 47. The weight supporting unit 48 may be a flexible shaft. One side of the weight supporting unit 48 may be mounted at the mounting unit 47, while the other side of the weight supporting unit 48 may be mounted at the moving bracket 54. The weight applied at the mounting unit 47 may be delivered to the moving bracket 54 through the weight supporting unit 48, and the weight delivered to the moving bracket 54 may be delivered to a floor surface through the rotating shaft 55, the connecting bracket 53, the hip joint 5, the frames 2 and 3, and the foot structure 8. As described above, a user may not feel the weight applied to the mounting unit 47. As the mounting unit 47 is provided to slide along the back rail 450, when a user does not perform a motion (e.g., bending the upper portion of the body of the user), the weight applied at the mounting unit 47 may not be directly applied to the user.

When a user wearing the walking assistance apparatus 1 moves the leg of the user in forward/backward directions, the rotating axis of the hip joint present at an inside the body of the user may not be in accord with the rotating shaft of the walking assistance apparatus 1. In such a case, the user wearing the walking assistance apparatus 1 may be uncomfortable to walk due to the discord of the rotating axes. However, as the rail unit 42 to which the hip joint 5 is connected is provided to slide along the extension direction of the waist fixing apparatus 4, the moving bracket 54 may be provided to be slide in the z-axis direction along the rail 422. The rail unit 42 may be provided to be spaced apart from the waist fixing apparatus 4. Thus, when the leg of the user moves, the offset that is present in between the rotating axis of the hip joint and the rotating shaft of the walking assistance apparatus 1 may be compensated. Further, the weight of the driving source provided at the walking assistance apparatus 1 may be delivered to a floor surface. Thus, a user may comfortably walk while not carrying the weight of the driving source. As the mounting unit at which the driving source is mounted is slidably provided in the vertical direction, even when a user performs a motion, such as bending the waist of the user, the weight may not be carried. According to some example embodiments of the present disclosure, the wearability of the walking assistance apparatus 1 may be enhanced, and the weight of the walking assistance apparatus 1 may be minimized, thereby enable the user to walk in a more comfortable manner.

The walking assistance apparatus 1 may be a walking assistance robot.

Although a few example embodiments of the present disclosure have been shown and described, it would be appreciated by those skilled in the art that changes may be made in these example embodiments without departing from the principles and spirit of the disclosure, the scope of which is defined in the claims and their equivalents.

What is claimed is:
1. A walking assistance apparatus, comprising:
   a waist fixing apparatus configured to be fixed to a waist of a user;
   a connecting guide mounted at the waist fixing apparatus, and configured to slide in an extension direction of the waist fixing apparatus and rotate on a rotating shaft extending in a vertical direction perpendicular to the extension direction;
   a rail unit mounted at one side of the connecting guide, the rail unit extending in a vertical direction; and
   a hip joint configured to slide along the rail unit.
2. The walking assistance apparatus of claim 1, wherein:
   the rail unit is spaced apart from the waist fixing apparatus.
3. The walking assistance apparatus of claim 1, wherein:
   the rail unit and the connecting guide are pivotally connected to each other.
4. The walking assistance apparatus of claim 1, further comprising:
   a rail extended in a length direction of the waist fixing apparatus; and
   a sliding unit configured to slide along the rail.

5. The walking assistance apparatus of claim 4, wherein:
the connecting guide is pivotally connected to the sliding unit.

6. The walking assistance apparatus of claim 4, wherein:
the connecting guide, the rail, and the sliding unit each are provided at both sides of the rail unit.

7. The walking assistance apparatus of claim 1, further comprising:
a moving bracket configured to slide along the rail unit; and
a connecting bracket configured to connect the moving bracket to the hip joint.

8. The walking assistance apparatus of claim 7, wherein:
the hip joint is fixed to the connecting bracket, and the connecting bracket is pivotally connected to the moving bracket.

9. The walking assistance apparatus of claim 7, further comprising:
a back rail at one side of the waist fixing apparatus and extending in the vertical direction; and
a mounting unit configured to slide along the back rail and mount a driving source thereon.

10. The walking assistance apparatus of claim 9, wherein:
one side of a weight supporting unit is mounted at the mounting unit, and
the other side of the weight supporting unit is mounted at the moving bracket.

11. The walking assistance apparatus of claim 10, wherein:
the weight supporting unit is a flexible shaft.

12. The walking assistance apparatus of claim 1, wherein:
a length of the waist fixing apparatus is configured to be adjusted by a belt adjusting unit.

13. The walking assistance apparatus of claim 12, wherein:
the waist fixing apparatus comprises a first waist fixing apparatus including a first gear unit at one side thereof, and
a second waist fixing apparatus including a second gear unit at one side thereof.

14. The walking assistance apparatus of claim 13, further comprising:
a third gear unit at the belt adjusting unit and configured to be teeth-coupled with the first gear unit and the second gear unit.

15. The walking assistance apparatus of claim 14, wherein:
the waist fixing apparatus has an accommodation unit provided with a back gear unit at an inner side surface thereof, and the back gear unit is configured to be selectively teeth-coupled with the third gear unit.

16. The walking assistance apparatus of claim 14, wherein:
rotation of the third gear unit is limited by the first and second gear units, and the first, second, and third gear units are teeth-coupled to each other.

17. The walking assistance apparatus of claim 14, wherein:
when the belt adjusting unit is rotated in one direction or the other, the first waist fixing apparatus and the second waist fixing apparatus draw near to each other or spaced apart from each other.

18. A walking assistance apparatus, comprising:
a waist fixing apparatus configured to be fixed to a waist of a user;
a rail unit mounted at the waist fixing apparatus through a connecting guide;
a hip joint configured to slide along the rail unit in a vertical direction perpendicular to an extension direction of the waist fixing apparatus;
a mounting unit at which a driving source is mounted; and
a weight supporting unit configured to connect the mounting unit to the hip joint such that a weight of the mounting unit is delivered to the hip joint,
wherein the connecting guide is configured to slide along a rail in an extension direction of the waist fixing apparatus, and the connecting guide and the waist fixing apparatus are pivotally connected to each other.

19. The walking assistance apparatus of claim 18, wherein:
the waist fixing apparatus is configured to adjust a length thereof.

20. The walking assistance apparatus of claim 18, further comprising:
a back rail extended in a vertical direction at one side of the waist fixing apparatus,
wherein the mounting unit is configured to slide along the back rail.

* * * * *